(12) United States Patent
Tanaka et al.

(10) Patent No.: US 8,293,893 B2
(45) Date of Patent: Oct. 23, 2012

(54) METHOD FOR PRODUCING 6-HYDROXYETHYLPENAM COMPOUND

(75) Inventors: Hideo Tanaka, Okayama (JP); Manabu Kuroboshi, Okayama (JP); Syoichi Tateyama, Okayama (JP); Takae Yamada, Tokushima (JP); Yutaka Kameyama, Osaka (JP)

(73) Assignee: Otsuka Chemical Co., Ltd., Osaka-Shi (JP)

( * ) Notice: Subject to any disclaimer, the term of this patent is extended or adjusted under 35 U.S.C. 154(b) by 387 days.

(21) Appl. No.: 12/530,307

(22) PCT Filed: Mar. 6, 2008

(86) PCT No.: PCT/JP2008/054057
§ 371 (c)(1),
(2), (4) Date: Nov. 18, 2009

(87) PCT Pub. No.: WO2008/111487
PCT Pub. Date: Sep. 18, 2008

(65) Prior Publication Data
US 2010/0113769 A1    May 6, 2010

(30) Foreign Application Priority Data
Mar. 9, 2007    (JP) .................................. 2007-59496

(51) Int. Cl.
*C07D 499/04*    (2006.01)
*C07D 499/861*    (2006.01)
(52) U.S. Cl. ...................................................... 540/310
(58) Field of Classification Search ................... 540/310
See application file for complete search history.

(56) References Cited

U.S. PATENT DOCUMENTS

| 4,287,181 | A | | 9/1981 | Kellogg | 424/114 |
|---|---|---|---|---|---|
| 4,304,779 | A | * | 12/1981 | Cavender et al. | 514/196 |
| 4,585,874 | A | | 4/1986 | Alpegiani et al. | 546/272 |
| 4,596,677 | A | | 6/1986 | Martel et al. | 260/245.2 R |
| 4,639,335 | A | | 1/1987 | Martel et al. | 540/304 |
| 4,713,450 | A | | 12/1987 | Alpegiani et al. | 540/214 |
| 4,762,921 | A | * | 8/1988 | Reed, III | 540/310 |
| 4,782,050 | A | * | 11/1988 | Chen | 514/192 |
| 4,868,296 | A | * | 9/1989 | Barth | 540/310 |
| 5,886,203 | A | * | 3/1999 | Jones et al. | 556/96 |

FOREIGN PATENT DOCUMENTS

| CN | 101220050 A | * | 7/2008 |
|---|---|---|---|
| JP | 56-65892 | | 6/1981 |
| JP | 59-112989 | | 6/1984 |
| JP | 61-171485 | | 8/1986 |
| JP | 2-25914 | | 6/1990 |

OTHER PUBLICATIONS

Miyashita, Bioorganic & Medicinal Chemistry Letters (1996), 6(3), 319-22.*

Kuroboshi, Manabu, et al., "Diastereoselective Synthesis of 6-BROM0-6-(1-Hydroxyethyl) Penicillanate by Cross-Coupling of 6,6-Dibromopenicillanate and Acetaldehyde Promoted With Grignard Reagents: Role of Amine Ligands," Heterocycles, vol. 73, Aug. 17, 2007, pp. 877-882, full text, particularly Table 1.
"Saishin Kouseizai Yoko," Novel Antibiotic Booklet, 9th Edition, Sakai, Katsuji, pp. 92-93 and 122-128, with partial English Translation (cited in the specification, p. 2).
DiNanno, Frank, et al., "Aldol Condensations of Regiospecific Penicillanate and Cephalosporanate Enolates. Hydroxyethylation at C-6 and C-7," J. Org. Chem., vol. 42, No. 18, 1977, pp. 2960-2965 (cited in the specification, p. 3).
Kim, Wan Joo, et al., "Stereospecific $C_6$-hydroxyethylation of the Penicillin Nucleus,"J. of Antibiotics, vol. 37, No. 10, Oct. 1984, pp. 1276-1277.

(Continued)

*Primary Examiner* — Mark Berch
(74) *Attorney, Agent, or Firm* — Kratz, Quintos & Hanson, LLP

(57) ABSTRACT

The present invention provides a method by which a 6-hydroxyethyl penam compound represented by General Formula (2) below can be produced with a high selectivity:

[Chem. 2]

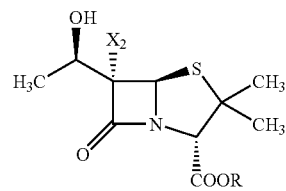

(2)

wherein R represents a hydrogen atom or a protective group for carboxylic acid and $X^2$ represents a halogen atom;
the method including the steps of reacting a Grignard reagent with a halogeno penam compound represented by General Formula (1) below:

[Chem. 1]

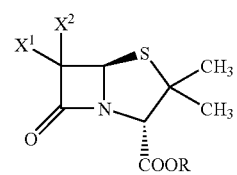

(1)

wherein R and $X^2$ are the same as above, and $X^1$ represents a halogen atom;
reacting the generated compound with an amine compound; and
further reacting the generated compound with acetaldehyde.

4 Claims, No Drawings

OTHER PUBLICATIONS

Kim, Wan Joo, et al., "Stereospecifric $C_6$-Hydroxyethylation of the Penicillin Nucleus," Bull. Korean Chem. Soc., vol. 5, No. 5, 1984, pp. 191-193.

Bedini, A., et al., "Synthesis and biological evaluation of 6-bromo-6-substituted panicillanic acid derivatives as β-lactamase inhibitors," II Farmaco, vol. 57, No. 8, 2002, pp. 663-669.

Fujimoto, Katsumi., et al., "From Penicillin to Penem and Carbapenem. VII. Synthesis and Antibacterial Activity of Penem Derivatives," Chem. Pharm. Bull., vol. 34, No. 3, 1986, pp. 999-1014.

Hirai, Koichi, et al., "From Penicillin to Penem and Carbapenem. 1. Racemization of 6,6-dibromo Secopenicillin, and Sythesis of 2-oxo Penam Derivative," Heterocycles, vol. 17, Jan. 1, 1982, pp. 201-207.

Yoshida, Akira, et al., "2-(Alkylthio)penem-3-carboxylic Acids. IV. Synthesis of (Hydroxyethyl)-azetidinone Precursors to 1-Thia Analogs of Thienamycin," Chem. Parm. Bull., vol. 29, No. 10, Oct. 1, 1981, pp. 2899-2909.

Goo, Yang Mo, et al., "Synthetic Studies on Penems and Carbapenems(IV). Practical Preparation of (3R, 4R-Acetoxy-3-[(1R)-1-hydroxyethyl]azetidin-2-one Derivatives from 6-Aminopenicillanic Acid," Bull. Korean Chem. Soc., vol. 8, No. 1, 1987, pp. 15-19.

Lee, Youn Young, et al. "Synthetic Studies on Penems and Carapenems (V). Preparation of 6-Acetylpenicillanate Derivatives," Bull. Korean Chem. Soc., vol. 8, No. 2, 1987, pp. 130-132.

Rosati, Robert L., et al. "Cephalosporins to Carbapenems: 1-Oxygenated Carbapenems and Carbapenems," J. Med. Chem. vol. 33, No. 1, 1990, pp. 291-297.

Leanza, W.J, et al. "An efficient synthesis of 2-substituted thio-6-hydroxyethyl-penem-3-carboxylic acids via 2-thioxopenams," Tetrahedron, vol. 39, No. 15, 1983, pp. 2505-2513.

Supplementary European Search Report dated Feb. 24, 2010.

* cited by examiner

METHOD FOR PRODUCING 6-HYDROXYETHYLPENAM COMPOUND

TECHNICAL FIELD

The present invention relates to a method for producing a 6-hydroxyethyl penam compound.

BACKGROUND ART

The 6-hydroxyethyl penam compound is represented by General Formula (2) below:

[Chem. 1]

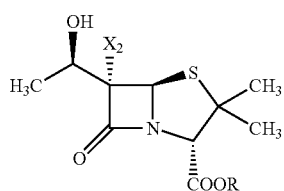

(2)

wherein R represents a hydrogen atom or a protective group for carboxylic acid, and $X^2$ represents a halogen atom.

The 6-hydroxyethyl penam compound is an important intermediate for synthesizing carbapenem antibiotics, including thienamycin, which is widely used as an injection medicine (Non-Patent Document 1).

The 6-hydroxyethyl penam compound represented by General Formula (2) comprises an asymmetrical carbon on the penam ring at 6-position at which a hydroxyethyl group and a halogen atom are substituted. Therefore, in the production of 6-hydroxyethyl penam compound, a method that achieves excellent stereoselectivity is required. Various studies have been conducted regarding the process by which a 6-hydroxyethyl penam compound is derived from a compound, such as the halogeno penam compound represented by General Formula (1) below having a skeleton in which 6-position is substituted with a halogen atom:

[Chem. 2]

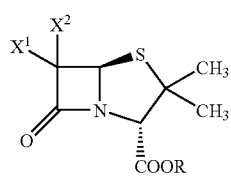

(1)

wherein R and $X^2$ are the same as above, and $X^1$ represents a halogen atom.

For example, a method employing a Grignard reagent is proposed. Non-Patent Document 2 discloses a method using methylmagnesium bromide, and Patent Document 1 discloses a method using ethylmagnesium bromide.

However, in these methods, it is impossible to produce the 6-hydroxyethyl penam compound represented by General Formula (2) with a high selectivity. For example, in the method of Non-Patent Document 2, the stereoselectivity of the objective compound is only about 70% (objective compound:byproduct=230:96.5). In the method of Non-Patent Document 1, the stereoselectivity of the objective compound is only about 62% (see Comparative Example 1 described below).

[Patent Document 1]
  Japanese Examined Patent Publication No. 1990-25914
[Non-Patent Document 1]
  "Saishin Kouseizai Yoko" (Novel Antibiotic Booklet), 9th Edition, Katsuji SAKAI, page 92
[Non-Patent Document 2]
  J. Org. Chem., 42, 2960 (1977)

DISCLOSURE OF THE INVENTION

Problem to be Solved by the Invention

An object of the present invention is to provide a method by which the 6-hydroxyethyl penam compound represented by General Formula (2) can be produced with a high selectivity.

Means for Solve the Problem

The present inventors conducted extensive research to solve the above problem, and found that the objective 6-hydroxyethyl penam compound represented by General Formula (2) can be produced with a high selectivity by the following procedure. An amine compound is used in the reaction of the halogeno penam compound represented by General Formula (1) with a Grignard reagent and acetaldehyde. In this reaction, the Grignard reagent, acetaldehyde and amine compound are reacted with the halogeno penam compound represented by General Formula (1) in a specific order. The present invention has been accomplished based on this finding.

The present invention provides the methods for producing 6-hydroxyethyl penam compound represented by General Formula (2) as described in Items 1 to 4 below.

Item 1. A method for producing a penam compound, wherein the penam compound is 6-hydroxyethyl penam compound represented by General Formula (2) below:

[Chem. 4]

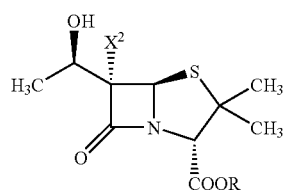

(2)

wherein R represents a hydrogen atom or a protective group for carboxylic acid, and $X^2$ represents a halogen atom,
  the method comprising the steps of:
  reacting a Grignard reagent with a halogeno penam compound represented by General Formula (1) below:

[Chem. 3]

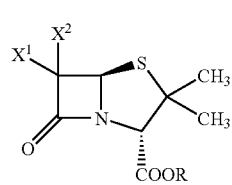

(1)

wherein R and $X^2$ are the same as above, and $X^1$ represents a halogen atom;

reacting the generated compound with an amine compound; and further reacting the generated compound with acetaldehyde.

Item 2. The method according to Item 1, wherein the amine compound is at least one member selected from the group consisting of monoamine compounds represented by General Formula (3) below:

[Chem. 5]

$$\begin{array}{c} R^1 \\ \diagdown \\ N-R^3 \\ \diagup \\ R^2 \end{array} \quad (3)$$

wherein $R^1$, $R^2$ and $R^3$ may be the same or different, and independently represent a $C_{1-4}$ alkyl group, $C_{3-8}$ cycloalkyl group or phenyl group, and $R^2$ and $R^3$ may be bonded to each other to form a $C_{2-6}$ alkylene group;

diamine compounds represented by General Formula (4) below:

[Chem. 6]

$$\begin{array}{c} R^4 \\ \diagdown \\ N-(CH_2)_l-N \\ \diagup \\ R^5 \end{array} \begin{array}{c} R^6 \\ \diagup \\ R^7 \end{array} \quad (4)$$

wherein $R^4$, $R^5$, $R^6$ and $R^7$ may be the same or different, and independently represent a hydrogen atom or a $C_{1-4}$ alkyl group, $R^4$ and $R^6$, and $R^5$ and $R^7$ may be bonded to each other to form a $C_{1-4}$ alkylene group, and l represents an integer of 2 to 4; and triamine compounds represented by General Formula (5) below:

[Chem. 7]

$$\begin{array}{c} R^8 \\ \diagdown \\ N-(CH_2)_m-N-(CH_2)_n-N \\ \diagup \\ R^9 \end{array} \begin{array}{c} R^{12} \\ | \\ R^{11} \end{array} \begin{array}{c} R^{10} \\ \diagup \\ R^{11} \end{array} \quad (5)$$

wherein $R^8$, $R^9$, $R^{10}$, $R^{11}$ and $R^{12}$ independently represent a $C_{1-4}$ alkyl group, and m and n independently represent an integer of 2 to 4.

Item 3. The method according to Item 1, wherein 1 to 10 mol of triamine compound is used per mole of Grignard reagent.

Item 4. The method according to Item 1, wherein the Grignard reagent is a $C_{1-4}$ alkyl magnesium halide.

Examples of the groups usable in the present invention are specified below.

There is no limitation to the protective groups for carboxylic acid, as long as they form a carboxylate. Examples thereof include methyl group, ethyl group, tert-butyl group and like $C_{1-6}$ alkyl groups; 2,2,2-trichloroethyl group and like $C_{1-6}$ haloalkyl groups; allyl group and like $C_{2-4}$ alkenyl groups; phenyl group, p-nitrophenyl group and like aryl groups; benzyl group, p-methoxybenzyl group, p-nitrobenzyl group, benzhydryl group, o-nitro benzhydryl group and like aryl-substituted alkyl groups; phenoxymethyl group and like aryloxy-substituted alkyl groups; trimethylsilyl, dimethyl-tert-butylsilyl group, diphenyl-tert-butylsilyl group and like substituted silyl groups; acetonyl groups; etc. The protective groups for carboxylic acid are esters that are known to be hydrolyzed in vivo and may be an acetoxymethyl group, a pivaloyloxymethyl group, phthalidyl group, etc., which have advantageous pharmacological characteristics.

Examples of halogen atoms include fluorine atom, chlorine atom, bromine atom and iodine atom.

Examples of $C_{1-4}$ alkyl groups include methyl group, ethyl group, n-propyl group, isopropyl group, n-butyl group, isobutyl group, sec-butyl group, tert-butyl group and like $C_{1-4}$ straight- or branched-chain alkyl groups.

Examples of $C_{3-8}$ cycloalkyl groups include cyclopropyl group, cyclobutyl group, cyclopentyl group, cyclohexyl group, cycloheptyl group and cyclooctyl group.

Examples of $C_{2-6}$ alkylene groups include ethylene group, trimethylene group, tetramethylene group, propylene group, ethylethylene group, pentamethylene group, hexamethylene group and like straight- or branched-chain $C_{2-6}$ alkylenes.

Examples of $C_{1-4}$ alkylene groups include methylene group, ethylene group, trimethylene group, tetramethylene group, propylene group, ethylethylene group and like straight- or branched-chain $C_{1-4}$ alkylenes.

In the present invention, the halogeno penam compound represented by General Formula (1) is first reacted with a Grignard reagent.

Any known Grignard reagents can be used in the present invention. Specific examples thereof include methylmagnesium chloride, methylmagnesium bromide, methylmagnesium iodide, ethylmagnesium chloride, ethylmagnesium bromide, ethylmagnesium iodide, n-propylmagnesium chloride, n-propylmagnesium bromide, n-propylmagnesium iodide, isopropylmagnesium chloride, isopropylmagnesium bromide, isopropylmagnesium iodide, n-butylmagnesium chloride, n-butylmagnesium bromide, n-butylmagnesium iodide, isobutylmagnesium chloride, isobutylmagnesium bromide, isobutylmagnesium iodide, tert-butylmagnesium chloride, tert-butylmagnesium bromide, tert-butylmagnesium iodide and like $C_{1-4}$ alkyl magnesium halides.

Among these Grignard reagents, $C_{1-2}$ alkyl magnesium halide is preferable, and ethylmagnesium chloride and ethylmagnesium bromide are particularly preferable.

The amount of Grignard reagent used is generally about 1 to 10 mol, and preferably about 1 to 4 mol per mole of the halogeno penam compound represented by General Formula (1).

The reaction is usually conducted in an appropriate solvent. Examples of the usable solvents include diethyl ether, tetrahydrofuran, dioxane and like chain or cyclic ethers; benzene, toluene, xylene, chlorobenzene, anisole and like aromatic hydrocarbons; etc. It is also possible to use these solvents as main solvents, and combine other solvents such as pentane, hexane, heptane, octane and like aliphatic hydrocarbons; and cyclopentane, cyclohexane, cycloheptane, cyclooctane and like cycloaliphatic hydrocarbons. The percentage of the main solvent per total solvent is generally not less than 80 vol. %, and preferably not less than 90 vol. %.

These solvents are generally used in an amount of about 0.5 to 200 liters, and preferably about 1 to 50 liters per 1 kg of the halogeno penam compound represented by General Formula (1).

The reaction proceeds in either a cold atmosphere or at room temperature, but it is preferable that the reaction be conducted in a cold atmosphere. The reaction is generally conducted at a temperature of −120 to 30° C., and preferably −80 to 0° C.; and the reaction is generally completed within about 0.1 to 3 hours, and preferably about 0.5 to 1 hour.

In the present invention, an amine compound is then coordinated with the compound generated by the reaction between the halogeno penam compound represented by General Formula (1) and the Grignard reagent (hereunder this compound may be referred to as "Compound A"). In the present invention, Compound A may be supplied to the subsequent reaction after isolating it from the reaction system. However, from the viewpoint of operation efficiency, it is preferable that Compound A be supplied to the subsequent reaction without being isolated.

Examples of amine compounds include monoamine compounds represented by General Formula (3), diamine compounds represented by General Formula (4), triamine compounds represented by General Formula (5), etc. These amine compounds may be used singly or in combination. Among these amine compounds, triamine compounds represented by General Formula (5) are preferable.

Examples of monoamine compounds represented by General Formula (3) include trimethylamine, triethylamine, tributylamine, ethyldiisopropylamine, dicyclohexylmethylamine, N-methyl piperidine, triphenylamine, etc. Among these monoamine compounds, triethylamine and ethyldiisopropylamine are preferable.

Examples of diamine compounds represented by General Formula (4) include ethylenediamine, propylenediamine, N,N,N',N'-tetramethylethylenediamine, N,N,N',N'-tetraethylethylenediamine, 1,4-diazabicyclo[2.2.2]octane, etc. Among these diamine compounds, N,N,N',N'-tetramethylethylenediamine and 1,4-diazabicyclo[2.2.2]octane are preferable.

Examples of triamine compounds represented by General Formula (5) include N,N,N',N'',N''-pentamethyldiethylenetriamine, N,N,N',N'',N''-pentaethyldiethylenetriamine, etc. Among these triamine compounds, N,N,N',N'',N''-pentamethyldiethylenetriamine is preferable.

These amine compounds are known compounds and easily available, or can be readily produced by a known method.

The amount of the amine compound used is generally about 1 to 10 mol, and preferably about 1 to 4 mol per 1 mole of the halogeno penam compound represented by General Formula (1), which is a starting material.

The amine compound may generally be used in an amount of about 1 to 10 mol, and preferably about 1 to 3 mol per 1 mole of the Grignard reagent; however, it is preferable that the amine compound be used in an almost equimolar ratio to the Grignard reagent.

The coordination of the amine compound to Compound A may proceed in either a cold atmosphere or at room temperature; however, conducting the coordination in a cold atmosphere is preferable. Specifically, the coordination is generally conducted at a temperature of −80 to 20° C., and preferably −78 to −40° C. The coordination is generally completed within about 0.1 to 3 hours, and preferably about 0.5 to 2 hours.

In the present invention, acetaldehyde is allowed to act on a compound to which an amine compound is coordinated to Compound A (hereunder, this compound may be referred to as "Compound B"). In the present invention, Compound B may be supplied to the subsequent reaction after being isolated from the reaction system; however, from the viewpoint of operation efficiency, Compound B is preferably supplied to the subsequent reaction without being isolated from the reaction mixture.

In the present invention, the acetaldehyde is generally used in an amount of about 1.5 to 10 mol, and preferably about 3 to 8 mol per mole of the halogeno penam compound represented by General Formula (1).

The reaction between Compound B and the acetaldehyde proceeds in either a cold atmosphere or at room temperature. However, it is preferable that the reaction be conducted in a cold atmosphere. Specifically, the reaction is conducted at a temperature of generally −80 to 20° C., and preferably −40 to 0° C.; and the reaction is completed within generally about 1 to 5 hours, and preferably about 1 to 3 hours.

The 6-hydroxyethyl penam compound represented by General Formula (2) produced through the above reaction can be extracted out from the reaction mixture as a substantially pure compound by conducting known isolation and purification treatments, which are standard extraction and crystallization treatments, after the completion of the reaction.

Effects of the Invention

The production method of the present invention allows the obtainment of a 6-hydroxyethyl penam compound represented by General Formula (2), which is a useful intermediate to produce carbapenem, with a high selectivity.

BEST MODE FOR CARRYING OUT THE INVENTION

The present invention is explained in detail below with reference to Examples and Comparative Example. However, the scope of the present invention is not limited to these examples.

Example 1

The halogeno penam compound represented by General Formula (1) (compound (1a): $X^1=X^2=Br$, $R=-CH_2(C_6H_5)_2$, 156 mg, 0.3 mmol) was placed in a two-necked flask, and the atmosphere in the flask was replaced with argon gas. Thereafter, 2.5 ml of tetrahydrofuran (THF) was placed in the flask and cooled to −78° C. Ethylmagnesium bromide (THF solution, 0.98 M, 0.50 ml, 0.49 mmol.) was added thereto, and stirred for 30 minutes.

Next, 0.11 ml (0.51 mmol) of N,N,N',N'',N''-pentamethyldiethylenetriamine was added thereto, and gradually heated to −40° C. over one hour, followed by stirring for 2 hours.

To the resulting reaction mixture, 2.0 ml of THF solution of acetaldehyde (0.08 ml, 1.5 mmol.) was added and gradually heated to 0° C. over 30 minutes, followed by stirring for 3 hours.

After the completion of the reaction, 1.5 ml of water and 3.0 ml of a saturated aqueous ammonium chloride solution were sequentially added. While diluting the reaction mixture with ethyl acetate, vacuum filtration with Celite®(Diatomaceous earth. filter aid) was conducted. After separating the filtrate, the water layer was extracted with ethyl acetate (10 ml×3 times). The obtained organic layers were combined, washed with saturated aqueous sodium chloride solution and dried over anhydrous sodium sulfate, after which the solvent was distilled off under a reduced pressure.

The residue was purified with silica gel column chromatography (toluene:ethyl acetate=10:1), and 126 mg (yield of 86%) of the objective 6-hydroxyethyl penam compound represented by General Formula (2) (in the compound (2a) shown below, $X^2=Br$, $R=-CH_2(C_6H_5)_2$) was obtained.

[Chem. 8]

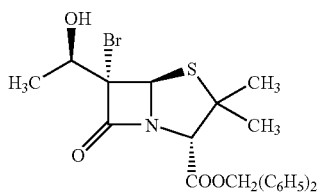

(2a)

In the above reaction, the production of stereoisomer (compound (2b)) represented by the formula below was confirmed.

[Chem. 9]

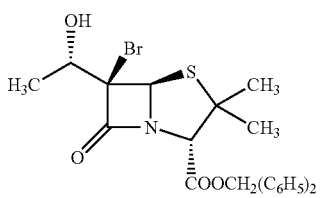

(2b)

The stereoselectivity of the reaction of the present invention was calculated based on the yields of compound (2a) and compound (2b). As a result, the stereoselectivity of the present invention reaction was 93%.

The physical properties of compound (2a) are shown below.

$^1$H-NMR(200 MHz,CDCl$_3$)δppm:
1.26 (s,3H), 1.28 (d,J=4.0 Hz,3H), 1.63 (s,3H), 2.40 (d,J=5.2 Hz,1H), 4.08-4.30 (m,1H), 4.61 (s,1H), 5.63 (s,1H), 6.94 (s,1H), 7.30-7.39 (m,10H)

$^{13}$C-NMR(500 MHz,CDCl$_3$)δppm:
17.96, 25.60, 33.52, 64.89, 67.17, 68.06, 71.87, 74.69, 78.54, 127.06, 127.34, 128.17, 128.28, 128.38, 128.59, 128.61, 128.98, 138.88, 138.95, 165.89, 169.03

IR(KBr):3471, 3063, 3033, 2978, 2931, 1783, 1746, 1496, 1455, 1373, 1256, 1179, 1020 cm$^{-1}$.

Examples 2 to 5 and Comparative Example 1

Compound (2a) was produced in the same manner as in Example 1, except that the amine compounds shown in Table 1 were used. In Comparative Example 1, amine compound was not used.

Table 1 shows the stereoselectivities of each example.

TABLE 1

| Example No. | Amine compound | Stereoselectivity (%) |
| --- | --- | --- |
| Ex. 2 | Triethylamine | 86 |
| Ex. 3 | Ethyldiisopropylamine | 82 |
| Ex. 4 | 1,4-diazabicyclo[2.2.2]octane | 84 |
| Ex. 5 | N,N,N',N'-tetramethylethylenediamine | 83 |
| Comp. Ex. 1 | None | 62 |

Example 6

Compound (2a) was produced in the same manner as in Example 1, except that triphenylamine was used as the amine compound. By using triphenylamine, compound (2a) was produced with a high selectivity.

The invention claimed is:

1. A method for producing a penam, wherein the penam is a 6-hydroxyethyl penam represented by Formula (2) below:

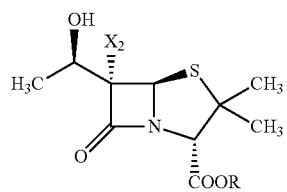

(2)

wherein R represents a hydrogen atom or a protective group for carboxylic acid, and X$^2$ represents a halogen atom, the method comprising the steps of:

adding a Grignard reagent to a halogeno penam represented by Formula (1) below:

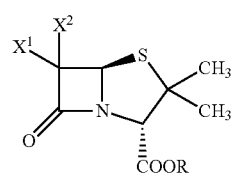

(1)

wherein R and X$^2$ are the same as above, and X$^1$ represents a halogen atom;

adding an amine to the generated compound; and further adding acetaldehyde to the generated compound.

2. The method according to claim 1, wherein the amine is at least one member selected from the group consisting of monoamines represented by Formula (3) below:

(3)

wherein R$^1$, R$^2$ and R$^3$ may be the same or different and independently represent a C$_{1-4}$ alkyl group, C$_{3-8}$ cycloalkyl group or phenyl group, and R$^2$ and R$^3$ may be bonded to each other to form a C$_{2-6}$ alkylene group;

diamines represented by Formula (4) below:

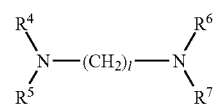

(4)

wherein R$^4$, R$^5$, R$^6$ and R$^7$ may be the same or different and independently represent a hydrogen atom or a C$_{1-4}$ alkyl group, R$^4$ and R$^6$, and R$^5$ and R$^7$ may be bonded to each other to form a C$_{1-4}$ alkylene group, and l represents an integer of 2 to 4; and triamines represented by Formula (5) below:
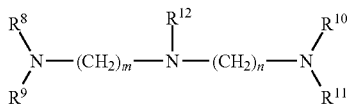
(5)
wherein $R^8$, $R^9$, $R^{10}$ $R^{11}$ and $R^{12}$ independently represent a $C_{1-4}$ alkyl group, and m and n independently represent an integer of 2 to 4.
3. The method according to claim 1, wherein 1 to 10 mol of amine is used per mole of Grignard reagent.
4. The method according to claim 1. wherein the Grignard reagent is a $C_{1-4}$ alkyl magnesium halide.
\* \* \* \* \*